US012558223B2

(12) United States Patent
Marrapode et al.

(10) Patent No.: US 12,558,223 B2
(45) Date of Patent: Feb. 24, 2026

(54) DEVICES AND METHODS FOR BONE HARVESTING

(71) Applicant: Warsaw Orthopedic, Inc., Warsaw, IN (US)

(72) Inventors: Matthew T. Marrapode, Boston, MA (US); Jeffrey N. Wickham, Ooltewah, TN (US); Fuad N. Mefleh, Thornton, CO (US); Jerald L. Redmond, Germantown, TN (US); Benjamin T. Reves, Memphis, TN (US); Christoph Scholtes, Louisville, CO (US); James B. Kelley, Thornton, CO (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/670,914

(22) Filed: Feb. 14, 2022

(65) Prior Publication Data

US 2023/0255775 A1    Aug. 17, 2023

(51) Int. Cl.
*A61F 2/28* (2006.01)
*A61B 10/02* (2006.01)
(Continued)

(52) U.S. Cl.
CPC .......... *A61F 2/2846* (2013.01); *A61B 10/025* (2013.01); *A61B 17/1635* (2013.01); *A61B 17/844* (2013.01); *A61F 2/30* (2013.01); *A61B 17/1666* (2013.01); *A61F 2002/2835* (2013.01); *A61F 2002/2839* (2013.01); *A61F 2002/285* (2013.01); *A61F 2002/30477* (2013.01);
(Continued)

(58) Field of Classification Search
CPC . A61B 17/1635; A61B 17/844; A61B 10/025; A61B 17/1666; A61B 17/864; A61B 17/8685; A61B 17/869; A61F 2002/30579; A61F 2002/3085
See application file for complete search history.

(56) References Cited

U.S. PATENT DOCUMENTS 2,685,877 A * 8/1954 Dobelle ................ A61F 2/3662
                                                      411/21
5,269,785 A   12/1993 Bonutti
                 (Continued)

FOREIGN PATENT DOCUMENTS

WO    WO 2009120969 A2    10/2009

OTHER PUBLICATIONS

Definition of monolithic retrieved from https://www.merriam-webster.com/dictionary/monolithic (Year: 2023).*
(Continued)

*Primary Examiner* — Dinah Baria
(74) *Attorney, Agent, or Firm* — Sorell, Lenna & Schmidt, LLP

(57) ABSTRACT

In some embodiments, a bone implant for percutaneous use is provided. The bone implant comprises a head, a body adjacent to the head and a tip opposite the head. At least the head, body or tip is configured to contact bone. An expandable member contacts at least one of the head, tip or body and is movable from an unexpanded configuration to an expanded configuration when deployed at a bone implant site. In some embodiments, a system for percutaneous bone harvesting is provided.

8 Claims, 11 Drawing Sheets

(51) Int. Cl.
  *A61B 17/16*        (2006.01)
  *A61B 17/84*        (2006.01)
  *A61F 2/30*         (2006.01)
(52) U.S. Cl.
  CPC .............. *A61F 2002/30579* (2013.01); *A61F 2002/30593* (2013.01); *A61F 2002/30672* (2013.01); *A61F 2002/3085* (2013.01)

(56)                References Cited

U.S. PATENT DOCUMENTS

| | | | |
|---|---|---|---|
| 5,380,334 A | 1/1995 | Torrie et al. | |
| 5,618,314 A | 4/1997 | Harwin et al. | |
| 5,948,000 A | 9/1999 | Larsen et al. | |
| 8,211,185 B2 * | 7/2012 | Linares ..................... | A61F 2/30 |
| | | | 623/23.12 |
| 8,668,668 B2 | 3/2014 | Bishop et al. | |
| 9,486,318 B2 * | 11/2016 | Forsell ..................... | A61F 2/36 |
| 9,980,761 B2 * | 5/2018 | Bonutti .............. | A61B 17/0218 |
| 10,751,161 B2 | 8/2020 | Diduch et al. | |
| 2008/0082165 A1 | 4/2008 | Wilson et al. | |
| 2008/0195115 A1 | 8/2008 | Oren et al. | |
| 2011/0112567 A1 | 5/2011 | Lenker et al. | |
| 2013/0053902 A1 * | 2/2013 | Trudeau ............. | A61B 17/8685 |
| | | | 606/313 |
| 2014/0188179 A1 | 7/2014 | McCormick | |
| 2016/0287301 A1 | 10/2016 | Mehl et al. | |
| 2019/0183525 A9 | 6/2019 | Ginn et al. | |
| 2019/0216456 A1 | 7/2019 | Schulz | |
| 2019/0231405 A1 * | 8/2019 | Redmond .......... | A61B 17/7055 |
| 2020/0253656 A1 * | 8/2020 | Scifert .............. | A61B 17/1642 |
| 2021/0113250 A1 * | 4/2021 | Major ............... | A61B 17/8685 |
| 2021/0228250 A1 * | 7/2021 | Suddaby .............. | A61B 17/869 |
| 2022/0087724 A1 * | 3/2022 | Schlenker .......... | A61B 17/7098 |
| 2022/0142679 A1 * | 5/2022 | Frock ................. | A61B 17/8875 |
| 2022/0280300 A1 * | 9/2022 | Dekel ................. | A61F 2/30749 |
| 2022/0280307 A1 * | 9/2022 | Haddad .............. | A61F 2/30749 |

OTHER PUBLICATIONS

Definition of adjacent retrieved from https://www.merriam-webster.com/dictionary/adjacent (Year: 2024).*
Definition of wings retrieved from https://www.merriam-webster.com/dictionary/wing (Year: 2024).*
International Search Report for PCT/US2023/012912 date of completion is May 11, 2023 (10 pages).

\* cited by examiner

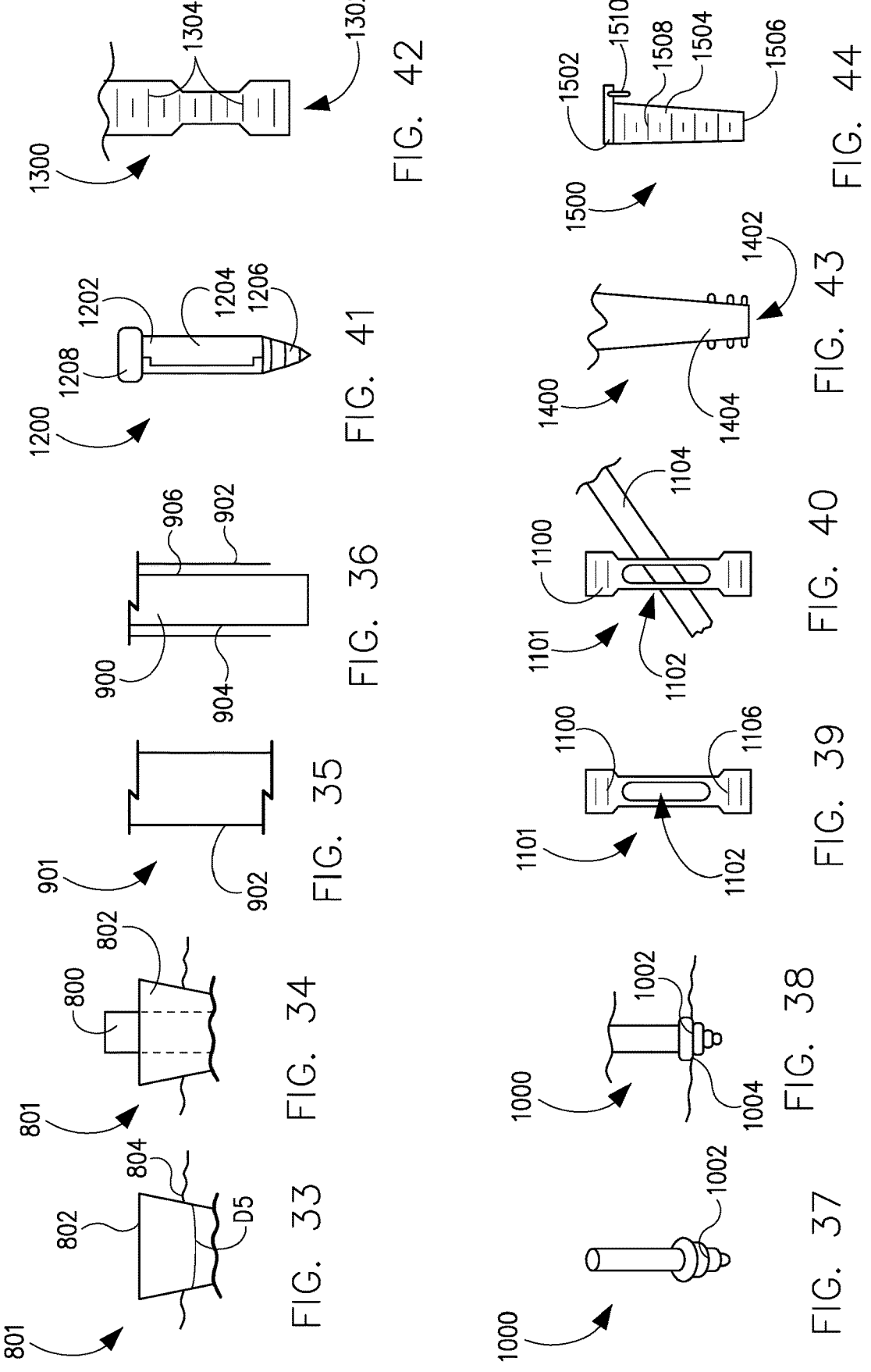

DEVICES AND METHODS FOR BONE HARVESTING

BACKGROUND

Surgical procedures can be performed with navigation technology that can assist in guiding and/or performing the procedures through computer and image guided assistance. During a procedure, for example, a minimally invasive surgical navigation guided procedure, a navigation reference frame can be attached to a surgical site, for example, the ilium of a patient via a percutaneous pin. The percutaneous pin can be attached to the ilium via disposal of the percutaneous pin within an opening created in the ilium by a surgeon.

When using autograft based fusion, the surgeon will typically harvest bone from the ilium as well, in the same general location where a percutaneous pin is typically attached. Bone harvesting from a patient is performed to extract and collect bone material to support spinal fusion. For minimally invasive procedures involving use of image guidance and percutaneous pin attachment, it is undesirable to create two openings along the pelvis to access bone for both harvesting and percutaneous pin attachment. If the surgeon is able to harvest bone from the existing opening created for the percutaneous pin, this can limit the number of wounds to the patient, since wounds require additional procedure management and can create the risk of perioperative and post-operative morbidity. However, harvesting of bone in the same area used for percutaneous pin attachment either before or during the procedure can cause the percutaneous pin to become destabilized, creating the risk of inaccuracy for the image guided procedure. If bone harvesting could be delayed to the end of the procedure, where image guidance is no longer needed, the hole created for the percutaneous pin limits the ability to use the same area for bone harvesting after removal of the percutaneous pin.

Therefore, devices, systems and methods are provided for both anchoring a navigation reference frame and for harvesting bone from one surgical site and/or one opening at the surgical site. Devices, systems and methods are also provided for percutaneous pin deployment, fixation and stability during a minimally invasive surgical navigation guided procedure where bone can also be harvested by the percutaneous pin from one surgical site and/or one opening at the surgical site. It would be beneficial to provide percutaneous pin fixation and stability at a surgical site before, during and/or after bone harvesting is performed. It would also be beneficial to provide a percutaneous pin that reduces the number of openings created in a patient during a minimally invasive surgical navigation guided procedure as well as during bone harvesting.

SUMMARY

Devices, systems and methods are provided for anchoring a navigation reference frame and for harvesting bone from one surgical site and/or one opening at the surgical site. Devices are also provided that employ percutaneous pin fixation and stability at a surgical site before, during and/or after bone harvesting is performed. Also provided are percutaneous pins that reduce the number of openings created in a patient during a minimally invasive surgical navigation guided procedure as well as during bone harvesting.

In some embodiments, a bone implant for percutaneous use is provided. The bone implant comprises a head, a body adjacent to the head and a tip opposite the head. At least the head, body or tip is configured to contact bone. An expandable member contacts at least one of the head, tip or body and is movable from an unexpanded configuration to an expanded configuration when deployed at a bone implant site.

In some embodiments, a bone implant for percutaneous use is provided. The bone implant comprises a head, a body adjacent to the head and a tip opposite the head. At least the head, body or tip is configured to contact bone. An anchoring element contacts at least one of the head, tip or body and is configured to fix the bone implant to a bone implant site.

In some embodiments, a surgical system for percutaneous bone harvesting is provided. The system comprises a bone implant comprising a head, a body adjacent to the head and a tip opposite the head, and an expandable member. The expandable member having an interior and an exterior, the interior of the expandable member configured to contact at least one of the head, tip or body, the exterior of the expandable member configured to contact bone at a bone implant site.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings.

FIG. 33 is a side view of one embodiment of a surgical system for percutaneous use;

FIG. 34 is a side view of the surgical system of FIG. 33;

FIG. 35 is a side view of one embodiment of a surgical system for percutaneous use;

FIG. 36 is a side view of the surgical system of FIG. 35;

FIG. 37 is a side view of one embodiment of a bone implant for percutaneous use;

FIG. 38 is a side view of the bone implant of FIG. 37;

FIG. 39 is a side view of one embodiment of a surgical system for percutaneous use;

FIG. 40 is a side view of the surgical system of FIG. 39;

FIG. 41 is a side view of one embodiment of a bone implant for percutaneous use;

FIG. 42 is a side view of one embodiment of a bone implant for percutaneous use;

FIG. 43 is a side view of one embodiment of a bone implant for percutaneous use;

FIG. 44 is a side view of one embodiment of a bone implant for percutaneous use;

Figure 1:
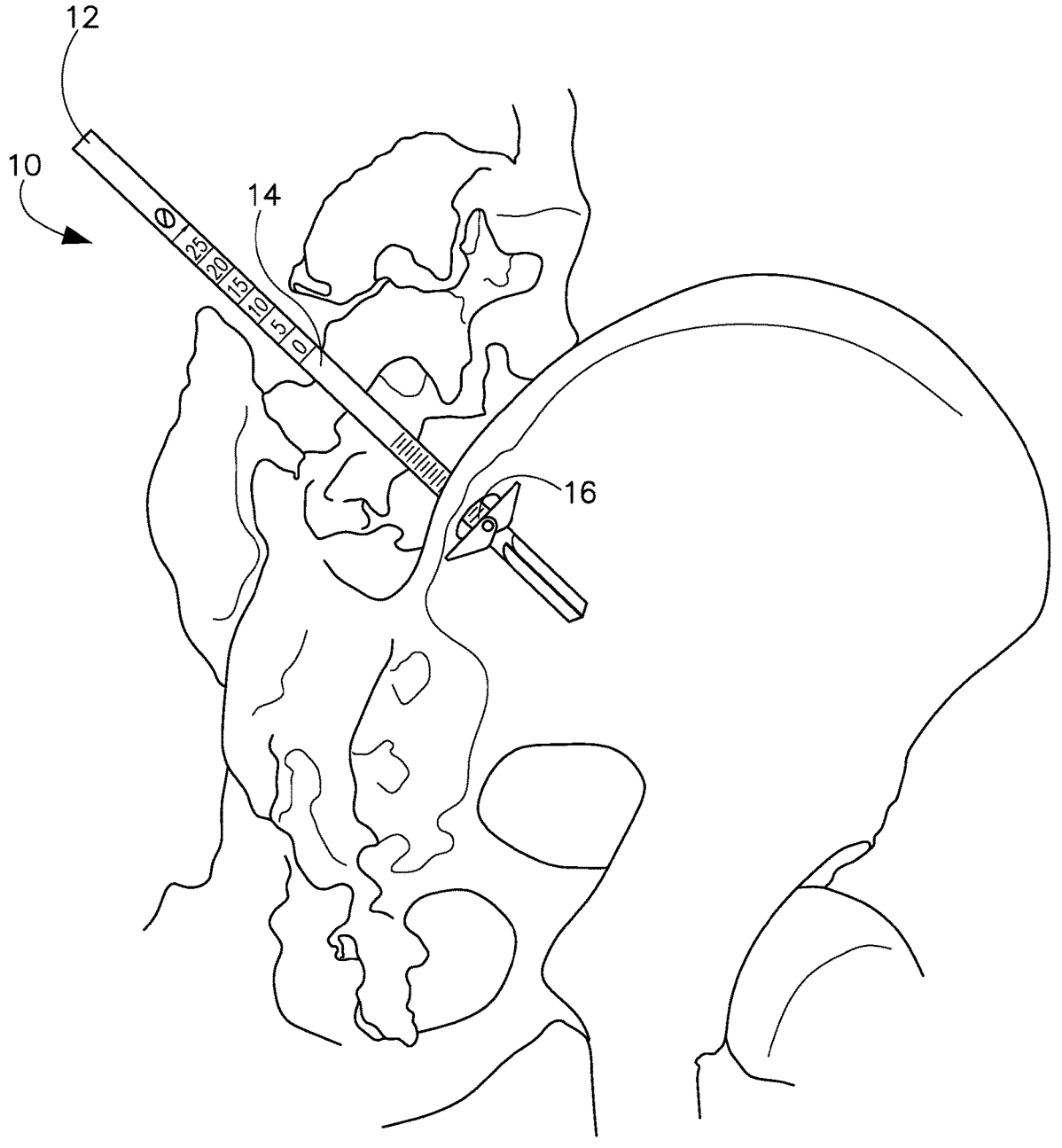
FIG. 1 is a perspective view of one embodiment of a bone implant for percutaneous use disposed at a bone implant site.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated device, and such further applications of the principles of the disclosure as described herein being contemplated as would normally occur to one skilled in the art to which the disclosure relates.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical representations are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

It is noted that, as used in this specification and the appended claims, the singular forms "a," "an," and "the," include plural referents unless expressly and unequivocally limited to one referent. Thus, for example, reference to "an allograft" includes one, two, three or more allografts.

The term "mammal" refers to organisms from the taxonomy class "mammalian," including but not limited to humans, other primates such as chimpanzees, apes, orang-utans and monkeys, rats, mice, cats, dogs, cows, horses, etc.

A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

The terms "treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," or "bone material" as used herein, refers to bone that is cortical, cancellous or cortico-cancellous of autogenous, allogeneic, xenogeneic, or transgenic origin.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "osteoconductive," as used herein, refers to the ability of a non-osteoinductive substance to serve as a suitable template or substance along which bone may grow.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a bone graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "demineralized," as used herein, refers to any material generated by removing mineral material from tissue, e.g., bone tissue. In certain embodiments, the demineralized compositions described herein include preparations containing less than 5%, 4%, 3%, 2% or 1% calcium by weight. Partially demineralized bone (e.g., preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," and "fully demineralized." In some embodiments, part or all of the surface of the bone can be demineralized. For example, part or all of the surface of the allograft can be demineralized to a depth of from about 100 to about 5000 microns, or about 150 microns to about 1000 microns. In some embodiments, part or all of the surface of the allograft can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns.

The term "demineralized bone matrix," as used herein, refers to any material generated by removing mineral material from bone tissue. In some embodiments, the DBM compositions as used herein include preparations containing less than 5%, 4%, 3%, 2% or 1% calcium by weight.

The term "superficially demineralized," as used herein, refers to bone-derived elements possessing at least about 90, 91, 92, 93, 94, 95, 96, 97, 98 or 99 weight percent of their original inorganic mineral content. The expression "partially demineralized" as used herein refers to bone-derived elements possessing from about 8 to about 90 weight percent of their original inorganic mineral content. In some embodiments, partially demineralized refers to bone-derived elements possessing from about 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88 to about 90 weight percent of their original inorganic mineral content. The expression "fully demineralized" as used herein refers to bone containing less than 8%, 7%, 6%, 5%, 4%, 3%, 2%, or 1% of its original mineral context.

The terms "pulverized bone", "powdered bone" or "bone powder" as used herein, refers to bone particles of a wide range of average particle size ranging from relatively fine powders to coarse grains and even larger chips.

The bone material can comprise bone fibers. Fibers include bone elements whose average length to average thickness ratio or aspect ratio of the fiber is from about 50:1 to about 1000:1. In overall appearance the fibrous bone elements can be described as elongated bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the elongated bone fibers are of irregular shapes including, for example, linear, serpentine or curved shapes. The elongated bone fibers are preferably demineralized, however, some of the original mineral content may be retained when desirable for a particular embodiment.

"Non-fibrous", as used herein, refers to elements that have an average width substantially smaller than the average thickness of the fibrous bone element or aspect ratio of less than from about 50:1 to about 1000:1. For example, allograft bone fibers will have a fiber shape, while the non-fibrous material will not have a fiber shape but will have a shape such as, for example, triangular prism, sphere, cube, cylinder, square, triangle, particle, powder, and other regular or irregular shapes.

Reference will now be made in detail to certain embodiments of the disclosure. The disclosure is intended to cover all alternatives, modifications, and equivalents that may be included within the disclosure as defined by the appended claims.

The headings below are not meant to limit the disclosure in any way; embodiments under anyone heading may be used in conjunction with embodiments under any other heading.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Bone Implant and Systems for Percutanous Use

In various embodiments, a bone implant 10 for percutaneous use is provided, as shown in FIGS. 1-15. The bone implant includes a percutaneous pin including a head 12, a body 14 adjacent to the head and a tip 16 opposite the head. At least the head, the body or the tip is configured to contact bone, for example, bone from the iliac crest of a patient, as shown in FIG. 1. The bone implant includes an expandable member 18 that contacts at least one of the head, the tip or the body, as shown in FIGS. 2-13. The expandable member is movable from an unexpanded configuration to an expanded configuration when deployed at a bone implant site, for example, a bone harvesting site. The bone implant is configured to anchor at the bone implant site before, during or after bone is harvested to provide stability and to prevent rotation of the bone implant when fixed to the bone implant site.

Figures 2, 3, 3A, 4, 5, 6, 7:
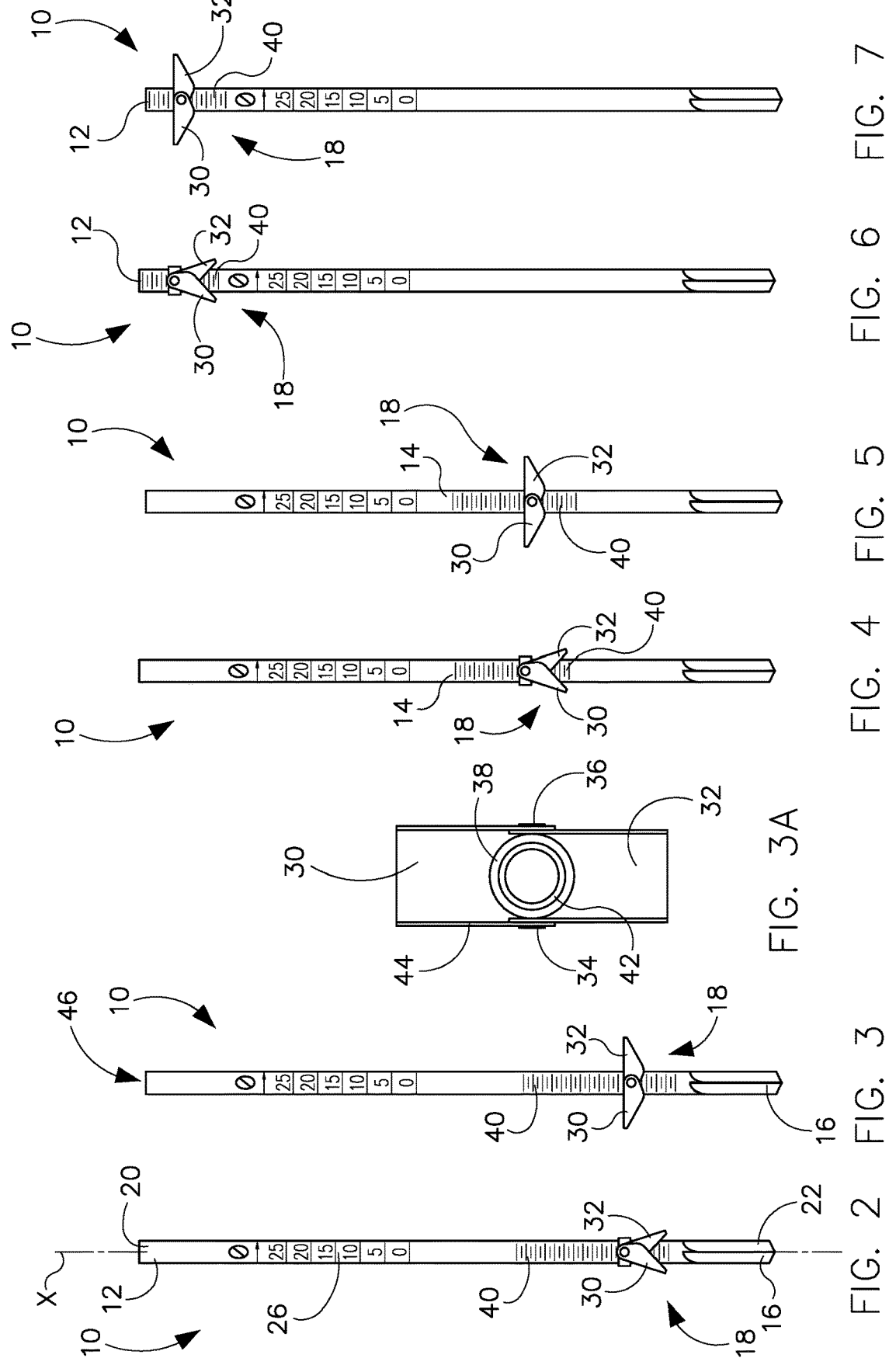
FIG. 2 is a side view of the bone implant of FIG. 1.
FIG. 3 is a side view of the bone implant of FIG. 1.
FIG. 3A is a top view of components of the bone implant of FIG. 1.
FIG. 4 is a side view of one embodiment of a bone implant for percutaneous use.
FIG. 5 is a side view of the bone implant of FIG. 4.
FIG. 6 is a side view of one embodiment of a bone implant for percutaneous use.
FIG. 7 is a side view of the bone implant of FIG. 6.
Figure 14:
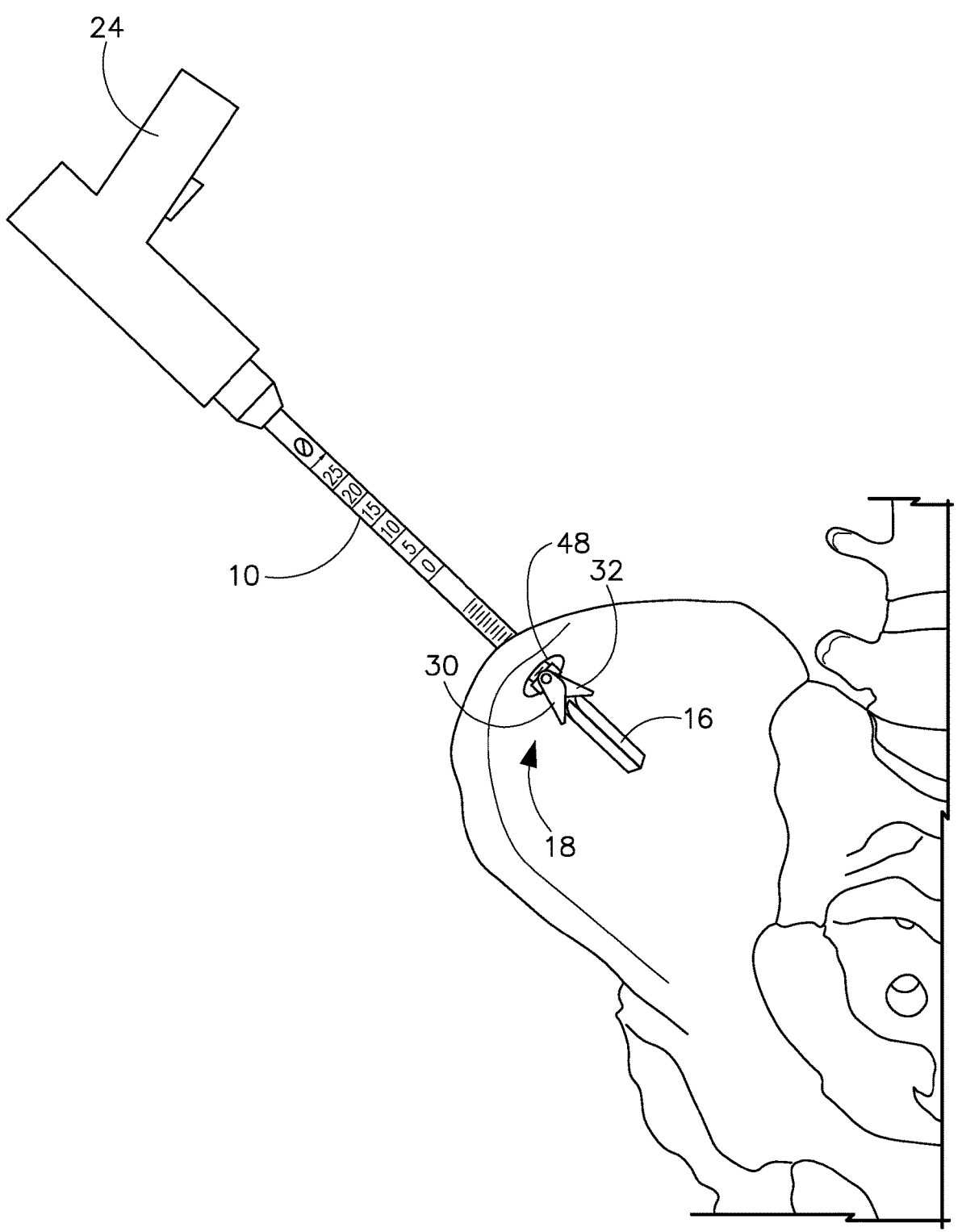
FIG. 14 is a perspective view of the bone implant of FIG. 1 disposed with a bone implant site.
Figure 56:
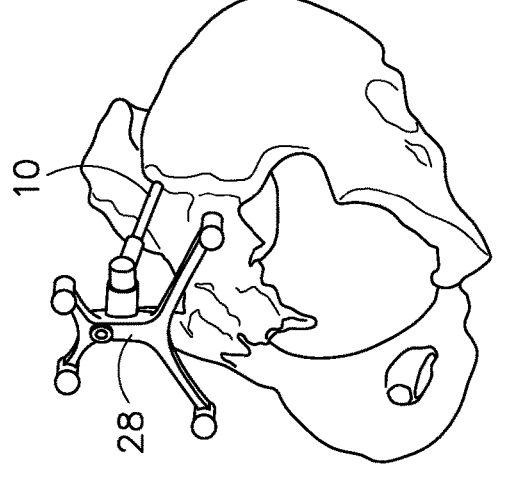
FIG. 56 is a perspective view of one embodiment of a percutaneous pin connected to a navigation component and a bone harvesting site.

The bone implant extends between an end 20 that includes the head and an end 22 that includes the tip. The bone implant is disposed along a longitudinal axis X, as shown in FIG. 2. The bone implant is monolithic and the head is configured to receive a surgical instrument, for example, a drill 24, as shown in FIG. 14. The surgical instrument may alternatively include a tap, a driver, a dilator and/or a trocar. The body of the bone implant can include indicia 26, for example, units of measurement to determine the depth of the bone implant when it is fixed in bone. The unit of measurement can be in inches, centimeters or millimeters. A navigation reference frame 28 can be attached to the body or the head of the bone implant when a minimally invasive surgical navigation guided procedure is performed at the same bone implant site as the bone harvesting, as shown in FIG. 56.

Figure 15:
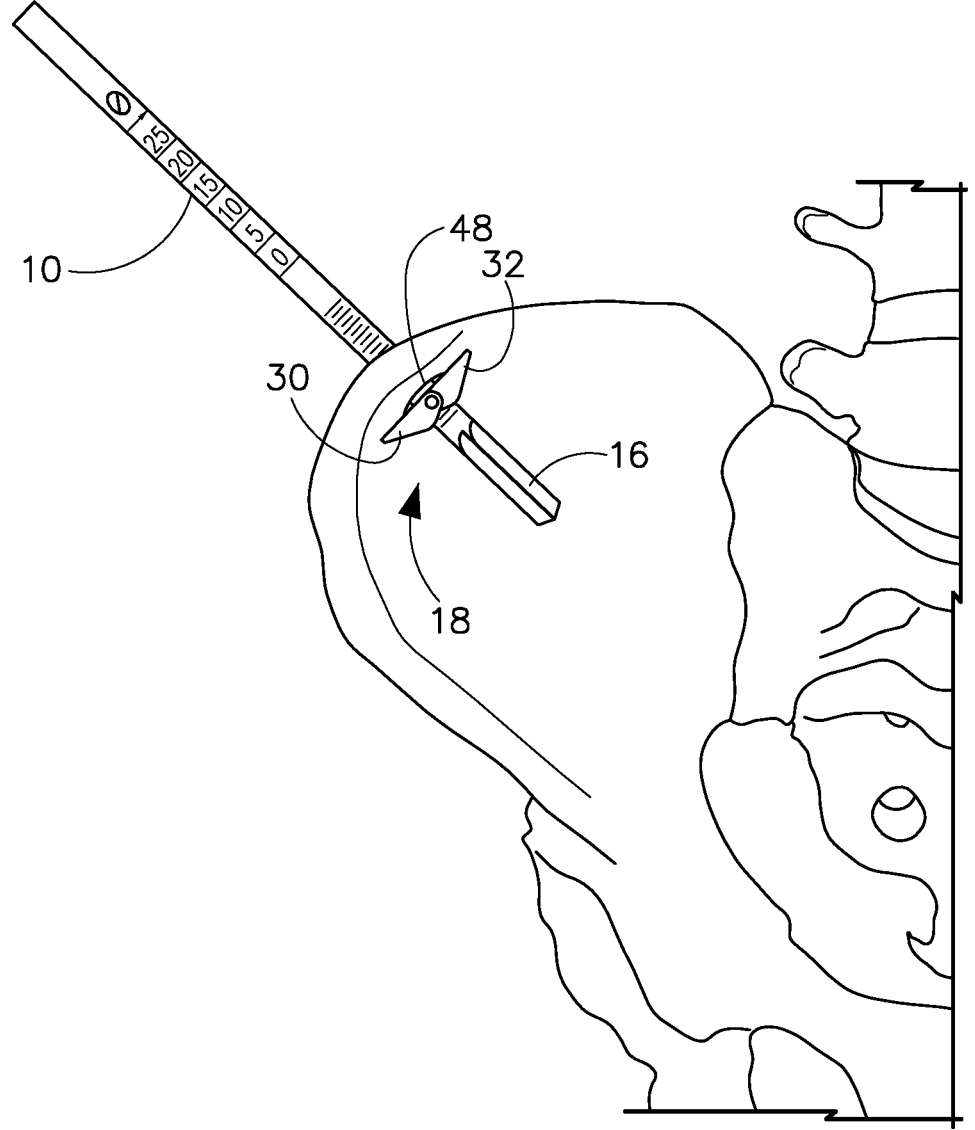
FIG. 15 is a perspective view of the bone implant of FIG. 1 fixed at bone implant site.

The expandable member includes at least one wing, for example, wings 30, 32, as shown in FIGS. 2-13. The wings are configured to anchor the bone implant at the bone implant site in the expanded configuration. In the expanded configuration, the wings are in an extended or open position, as shown in FIG. 15. In the unexpanded configuration, the wings are in a retracted or closed position, as shown in FIG. 14. The wings engage through tabs 34, 36 of a threaded nut 38, as shown in FIG. 3A. The threaded nut is configured for threaded engagement with threaded portions 40 of the bone implant. Translation of the bone implant though a threaded opening 42 in the threaded nut coupled with tension from a spring 44 engaged with the threaded nut and wings, moves the wings from the unexpanded to the expanded configuration, as shown in FIGS. 2, 3 and 3A.

Figures 8, 9, 10, 11, 12, 13:
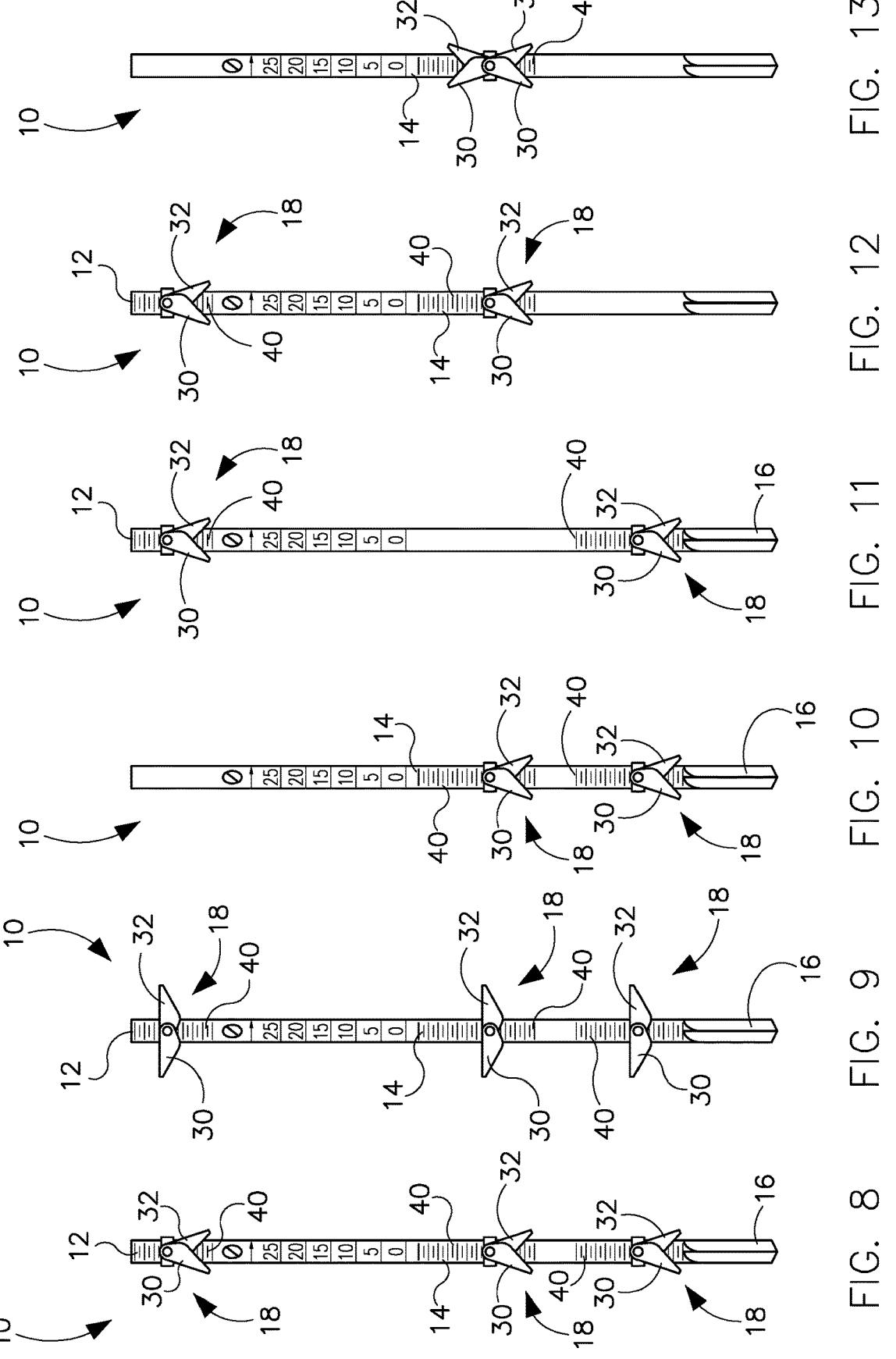
FIG. 8 is a side view of one embodiment of a bone implant for percutaneous use.
FIG. 9 is a side view of the bone implant of FIG. 8.
FIG. 10 is a side view of one embodiment of a bone implant for percutaneous use.
FIG. 11 is a side view of one embodiment of a bone implant for percutaneous use.
FIG. 12 is a side view of one embodiment of a bone implant for percutaneous use.
FIG. 13 is a side view of one embodiment of a bone implant for percutaneous use.

The expandable member, for example the wings, are configured to contact the bone implant at the head, the body and/or the tip, as shown in FIGS. 2-13. FIGS. 2 and 3 depict the wings contacting the tip of the bone implant and the wings are shown in the unexpanded (FIG. 2) and the expanded (FIG. 3) configurations. FIGS. 4 and 5 depict the wings contacting the body of the bone implant and the wings are shown in the unexpanded (FIG. 4) and the expanded (FIG. 5) configurations. FIGS. 6 and 7 depict the wings contacting the head of the bone implant and the wings are shown in the unexpanded (FIG. 6) and the expanded (FIG. 7) configurations. FIGS. 8 and 9 depict the wings contacting the head, the body and the tip of the bone implant and the wings are shown in the unexpanded (FIG. 8) and the expanded (FIG. 9) configurations. FIG. 10 depicts the wings contacting the body and the tip of the bone implant. FIG. 11 depicts the wings contacting the head and the tip of the bone implant. FIG. 12 depicts the wings contacting the head and the body of the bone implant.

The bone implant can include a plurality of expandable members. FIG. 13 depicts the bone implant including two pairs of wings contacting the body. In some embodiments, the bone implant can include 2 to 10 pairs of wings contacting the head, the body and/or the tip. The expandable member can include cutting flutes, spikes, flanges, rods, claws, anchors, plates, threading and/or wedges.

Figure 57:
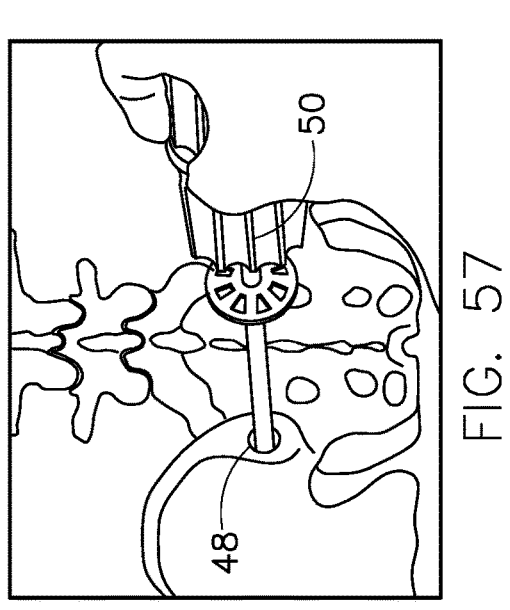
FIG. 57 is a perspective view of one embodiment of a bone harvesting tool for harvesting bone at a bone harvesting site.
Figure 59:
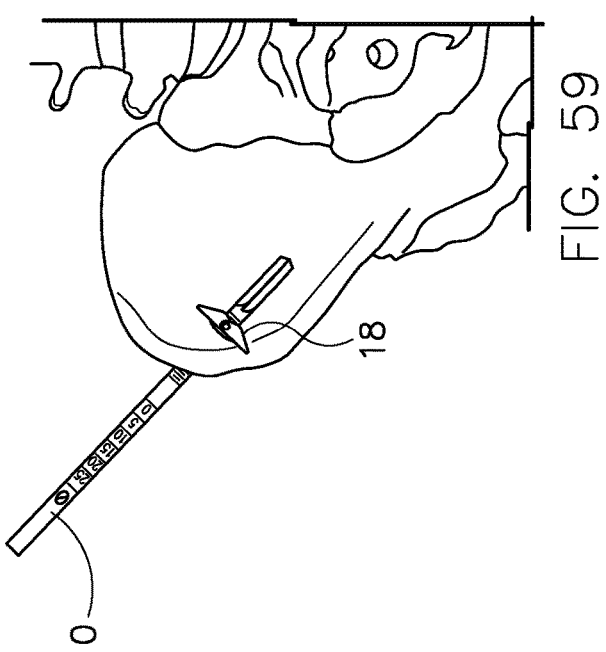
FIG. 59 is a perspective view of one embodiment of a percutaneous bone implant fixed with an opening at a bone harvesting site.
Figure 58:
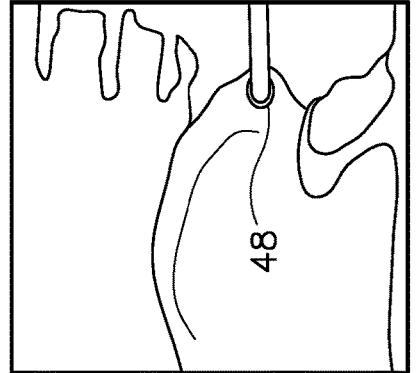
FIG. 58 is a perspective view of one embodiment of an opening disposed at the bone harvesting site.

The body of the bone implant is cannulated 46 such that the bone implant can be implemented to harvest bone at the bone implant site, as shown in FIG. 3. Portions or the entirety of the bone implant can have a diameter that is greater than a diameter of an opening 48 (shown in FIGS. 14 and 15) at the bone implant site to facilitate bone implant fixation with the opening. In some embodiments, the bone implant is anchored to the bone implant site after a percutaneous pin (not shown) has been removed from the opening at the bone implant site after bone has been harvested. In some embodiments, the opening at the bone implant site is created via a bone harvesting device, for example, a trocar 50, as shown in FIG. 57. In some embodiments, the bone implant is a temporary bone implant and is configured to anchor at the bone implant site for about 1 minute to about 59 minutes, 1 hour to about 23 hours or 1 day to about 365 days. In some embodiments, the bone implant is permanently left in the bone implant site.

Figures 16, 17, 18, 19, 20:
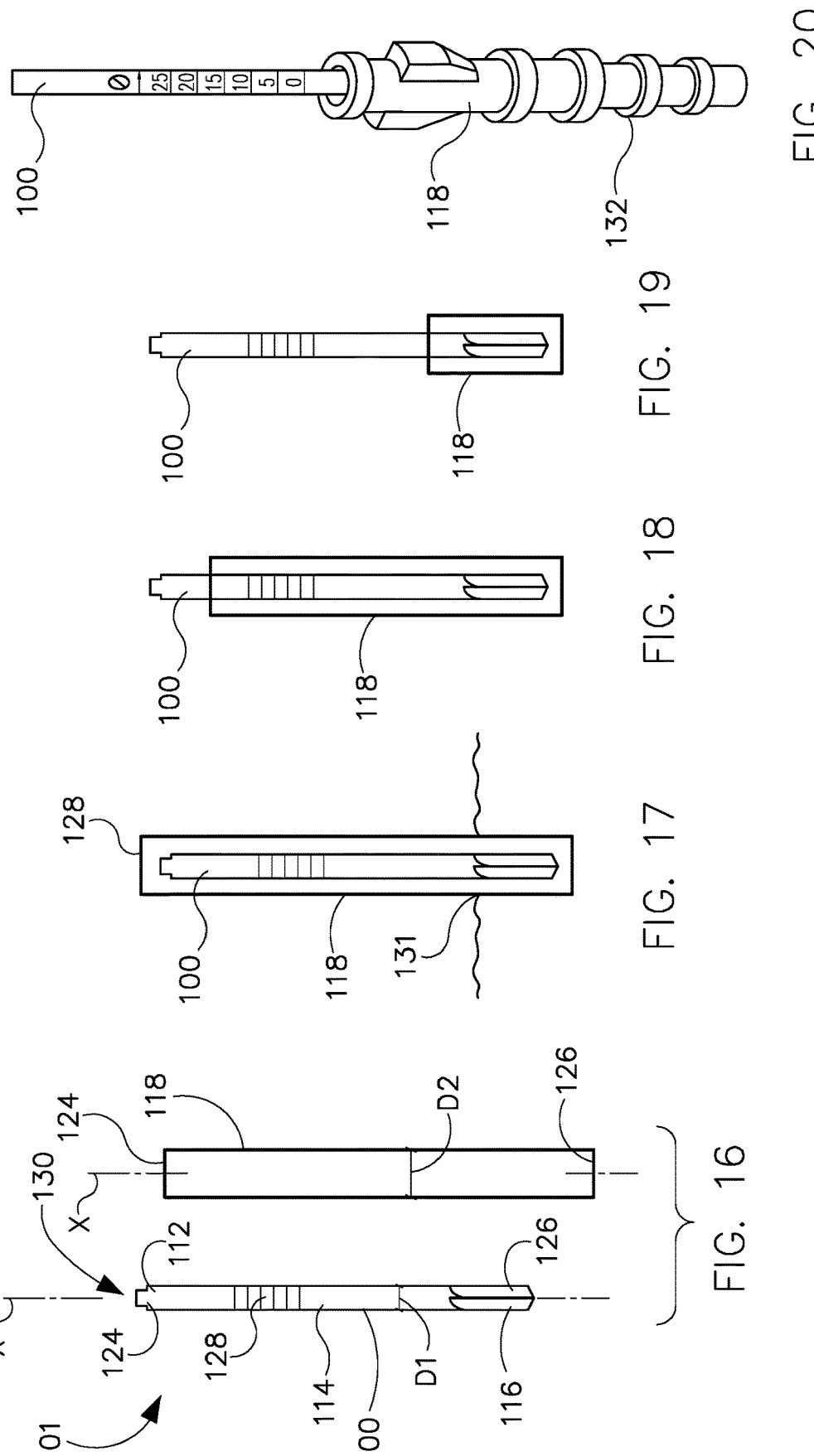
FIG. 16 is a side view of one embodiment of a surgical system for percutaneous bone harvesting.
FIG. 17 is a side view of the surgical system of FIG. 16.
FIG. 18 is a side view of the surgical system of FIG. 16.
FIG. 19 is a side view of the surgical system of FIG. 16.
FIG. 20 is a side view of one embodiment of a surgical system for percutaneous bone harvesting.

FIGS. 16-20 depict a surgical system 101 for percutaneous bone harvesting. The surgical system includes a bone implant 100. The bone implant includes a percutaneous pin that comprises a head 112, a body 114 adjacent to the head and a tip 116 opposite the head, as shown in FIG. 16. An expandable member 118 is provided having an interior 120 and an exterior 122. The interior of the expandable member is configured to contact at least one of the head, tip or body, and the exterior of the expandable member is configured to contact bone at a bone implant site. Similar to bone implant 10 described above and shown in FIGS. 1-15, the bone implant is configured to anchor at the bone implant site before, during or after bone is harvested to provide stability and to prevent rotation of the bone implant when fixed to the bone implant site.

The bone implant extends between an end 124 that includes the head and an end 126 that includes the tip. The bone implant is disposed along longitudinal axis X, as shown in FIG. 16. The bone implant is monolithic and the head is configured to receive a surgical instrument, for example, drill 24, similar to bone implant 10 described above. The body of the bone implant can include indicia 128. Navigation reference frame 28 can be attached to the body or the head of the bone implant, as shown in FIG. 56, similar to bone implant 10 described above. The bone implant is cannulated 130 such that the bone implant can be implemented to harvest bone at the bone implant site, as shown in FIG. 16.

The expandable member, for example, a sheath is configured to contour at least a portion of the bone implant. The expandable member extends between an end 124 and an end 126. The expandable member is disposed along the same longitudinal axis X as the bone implant, as shown in FIG. 16. At least end 124 includes an opening 128 such that the bone implant can be disposable within the expandable member, as shown in FIG. 17. The interior of the expandable member has a diameter D2 that is larger than a diameter D1 of at least a portion of the bone implant, as shown in FIG. 16. Diameter D2 is larger than diameter D1 such that at least a portion of the bone implant is disposed within the interior of the expandable member to cause the exterior of the expandable to be movable from an unexpanded configuration to an expanded configuration when deployed at a bone implant site. In the unexpanded configuration, the expandable member is not in engagement with the bone implant. The expandable member is configured for disposal and deployment within an opening 131 at the bone implant site, as shown in FIG. 17, similar to opening 48, shown in FIGS. 14 and 15 such that the bone implant can be fixed with the opening in the expandable configuration.

At least a portion of the bone implant is disposed within the interior of the expandable member, as described herein. FIG. 17 depicts the bone implant completely disposed within the interior. FIG. 18 depicts the body and the tip disposed within the interior. FIG. 19 depicts the tip disposed within the interior. FIG. 20 depicts portions of the expandable member being threaded 132. The expandable member can be threaded to enhance fixation with tissue at the bone implant site. In some embodiments, all of the expandable member is threaded. In some embodiments, all of portions of the expandable member can include barbs, raised elements and/or spikes to facilitate fixation with tissue at the bone implant site.

FIGS. 21-55 depict various bone implants and/or surgical systems, similar to bone implant 10, bone implant 100 and surgical system 101 described above, that are configured for percutaneous use. The bone implants include anchoring elements, including, but not limited to expandable members that are configured to fix the bone implant to a bone implant site before, during or after bone is harvested to provide stability and to prevent rotation of the bone implant when fixed to the bone implant site.

Figures 21, 22, 23, 24, 25, 26, 27, 28, 29, 30, 31, 32:
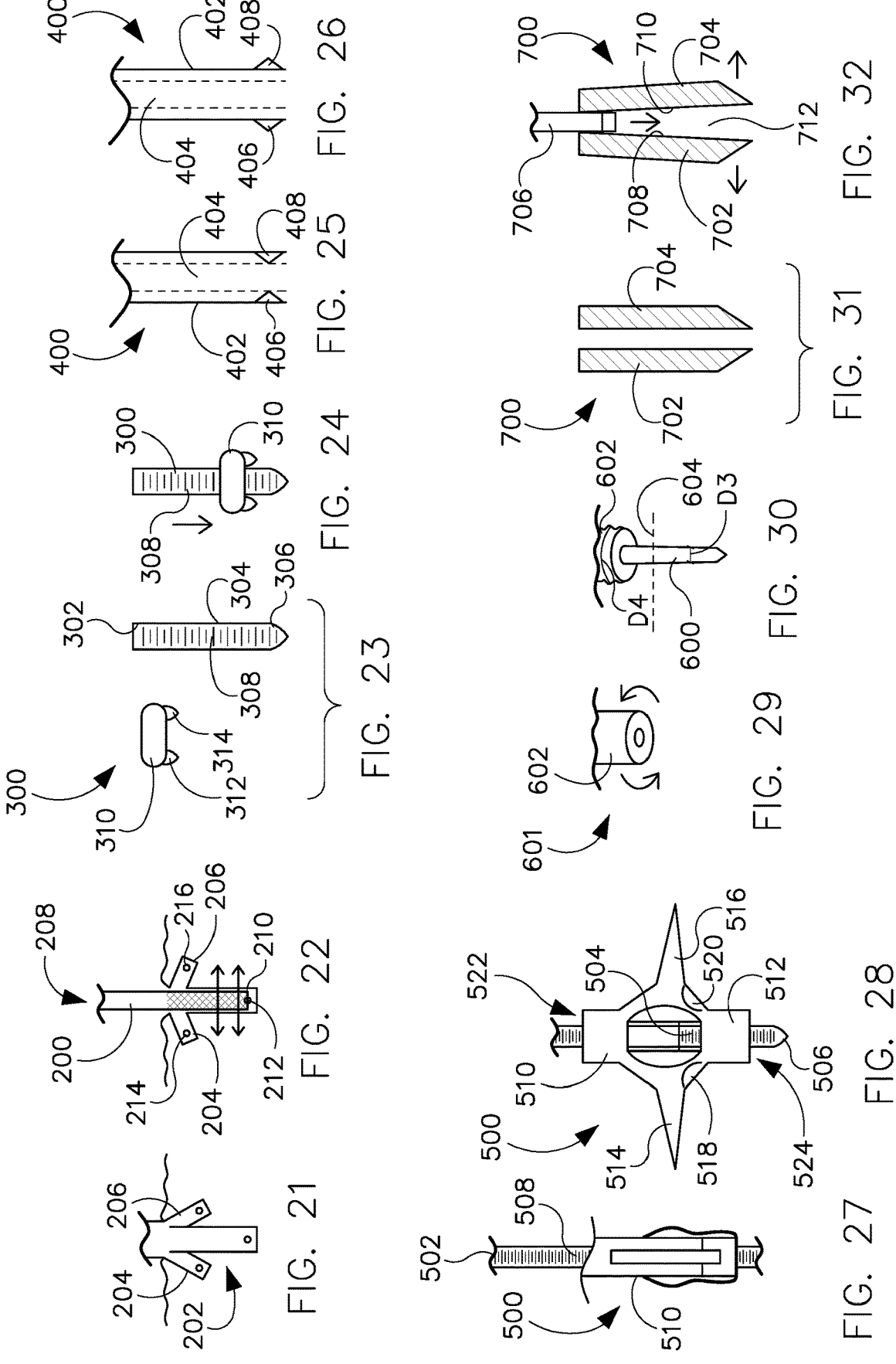
FIG. 21 is a side view of one embodiment of a bone implant for percutaneous use.
FIG. 22 is a side view of the bone implant of FIG. 21.
FIG. 23 is a side view of one embodiment of a bone implant for percutaneous use.
FIG. 24 is a side view of the bone implant of FIG. 23.
FIG. 25 is a side view of one embodiment of a bone implant for percutaneous use.
FIG. 26 is a side view of the bone implant of FIG. 25.
FIG. 27 is a side view of one embodiment of a bone implant for percutaneous use.
FIG. 28 is a side view of the bone implant of FIG. 27.
FIG. 29 is a side view of one embodiment of a surgical system for percutaneous use.
FIG. 30 is a side view of the surgical system of FIG. 29.
FIG. 31 is a side view of one embodiment of a bone implant for percutaneous use.
FIG. 32 is a side view of the bone implant of FIG. 31.

FIGS. 21-22 depict a bone implant 200, similar to bone implant 10 described above with regard to FIGS. 1-15. The bone implant, for example, a percutaneous pin includes an expandable member 202, similar to expandable member 18 described above with regard to bone implant 10. The expandable member is movable from an unexpanded configuration (FIG. 21) to an expanded configuration (FIG. 22) when deployed at a bone implant site, for example, a bone harvesting site to fix the bone implant to the bone implant site. The expandable member includes wings 204, 206 that are configured to anchor the bone implant at a bone implant site when in the expanded configuration. The bone implant is cannulated 208 and is configured for collecting bone material from the bone implant site. A tip 210 of the bone implant includes an opening 212 and the wings include openings 214, 216 configured to collect bone during harvesting.

FIGS. 23-24 depict a bone implant 300, similar to bone implant 100 described above with regard to FIGS. 16-20. The bone implant, for example, a percutaneous pin comprises a head 302, a body 304 adjacent to the head and a tip 306 opposite the head. The bone implant includes threads 308 disposed along at least the body and the tip. The bone implant includes an anchoring element, for example, a cap 310 including teeth 312, 314. The cap is configured for engagement with the bone implant such that the cap is translatable relative to the bone implant to fix the bone implant to the bone implant site. The cap can be hammered over the bone implant so that the cap translates in a downward direction to the tip of the bone implant for fixation with tissue at the bone implant site. In some embodiments, the anchoring device does not increase post operative pain in a patient. In some embodiments the bone implant can be cannulated to collect bone material from the bone implant site.

FIGS. 25-26 depict a bone implant 400, similar to bone implant 10 described above with regard to FIGS. 1-15 and bone implant 100 described above with regard to FIGS. 16-20. The bone implant includes a sleeve 402, an inner shaft 404 and an expandable member, similar to expandable member 18 described above. The expandable member includes a wings 406, 408 that are movable from an unexpanded configuration (FIG. 25) to an expanded configuration (FIG. 26) when deployed at a bone implant site. The wings are moved into the expanded configuration when the inner shaft engages with the wings. In some embodiments the bone implant can be cannulated to collect bone material from the bone implant site.

FIGS. 27-28 depict a bone implant 500, similar to bone implant 10 described above with regard to FIGS. 1-15. The bone implant includes a percutaneous pin comprising a head 502, a body 504 adjacent to the head and a tip 506 opposite the head. The bone implant includes threads 508 disposed along the bone implant. A threaded sleeve 510 and threaded nut 512 are configured for engagement with the bone implant. A portion of the sleeve includes an anchoring element, for example, wings 514, 516. The wings are monolithic with the sleeve and engageable with resilient arms 518, 520 of the nut. The wings are configured to be movable from an unexpanded configuration (FIG. 27) to an expanded configuration (FIG. 28) when deployed at a bone implant site, for example, a bone harvesting site. The wings are moveable from the unexpanded configuration to the expanded configuration when the bone implant is translated through a threaded passageway 522 of the sleeve and into a threaded passageway 524 of the nut such that the resilient arms move the wings into the expanded configuration.

FIGS. 29-30 depict a surgical system 601 including a bone implant 600, for example, a percutaneous pin, similar to the bone implants described above. The bone implant is configured as an anchoring element to fix the bone implant at a bone implant site. The system includes a bone harvesting device, for example, a cannulated trocar assembly 602. The bone implant includes a diameter D3 that is smaller than a diameter D4 of the cannulated trocar assembly, as shown in FIG. 30 such that the cannulated trocar assembly can engage with the bone implant. For example, the bone implant is inserted into the bone implant site and the cannulated trocar assembly is disposed over the bone implant such that harvesting and fixation can occur at the same opening 604 at a bone implant site.

FIGS. 31 and 32 depict a bone implant 700, for example, a percutaneous pin, similar to the bone implants described above. The bone implant includes an expandable member, for example, a pair of expandable spring flutes 702, 704 that are movable from an unexpanded configuration (FIG. 31) to an expanded configuration (FIG. 32) after bone has been harvested from a bone implant site. After bone has been harvested from the bone implant site, a through shaft 706 moves the expandable spring flutes from the unexpanded configuration to the expanded configuration when the through shaft engages interior surfaces 708, 710 of the expandable spring flutes and translates in a downward direction through a passageway 712 located in between the expandable spring flutes.

FIGS. 33-34 depict a surgical system 801 including a bone implant 800, for example, a percutaneous pin, similar to the bone implants described above. The system includes an anchoring element, for example, a tapered sleeve 802. The tapered sleeve includes a diameter D5, as shown in FIG. 33. The diameter D5 of the tapered sleeve is configured to engage a hole 804 formed in the bone implant site created by a bone harvesting device, for example, a trocar. The bone implant is configured for disposal within the tapered sleeve and the tapered sleeve is configured to fix the bone implant at the bone implant site.

FIGS. 35-36 depict a surgical system 901 including a bone implant 900, for example, a percutaneous pin, similar to the bone implants described above. The system includes an anchoring element, for example, a sleeve 902 to stabilize sides 904, 906 of the bone implant during fixation of the bone implant with a bone implant site.

FIGS. 37-38 depict a bone implant 1000, for example, a percutaneous pin, similar to the bone implants described above. The bone implant includes an anchoring element, for example, threaded tip 1002. The threaded tip is configured to screw into a hole 1004 formed from a bone harvesting device, for example, a trocar. The threaded tip is configured to fix the bone implant at the bone implant site. In some embodiments, all or portions of the bone implant are threaded. In some embodiments, the bone implant is alternatively a threaded sleeve configured for engagement with a percutaneous pin.

FIGS. 39-40 depict a surgical system 1101 including a bone implant 1100, for example, a percutaneous pin, similar to the bone implants described above. The bone implant is configured as an anchoring element and includes a slot 1102 configured for disposal of a bone harvesting device, for example, a trocar 1104. The bone implant includes threading 1106 and the bone implant is hollow. The bone implant enables harvesting of bone via the trocar while fixation of the bone implant is maintained at a bone implant site.

FIG. 41 depicts a bone implant 1200, for example, a percutaneous pin, similar to the bone implants described above. The bone implant includes a head 1202, a body 1204 adjacent to the head and a threaded tip 1206 opposite the head. The threaded tip is configured as an anchoring element to fix the bone implant at a bone implant site. The implant includes a bone harvesting assembly, for example, a plug catheter 1208 configured to shave and collect bone from the bone implant site. The bone implant is configured to harvest bone and fix the bone implant at the bone implant site.

FIG. 42 depicts a bone implant 1300, for example, a percutaneous pin, similar to the bone implants described above. The bone implant is hollow/cannulated 1302 and includes threading 1304. The bone implant is configured as an anchoring element to fix the bone implant at a bone implant site. In some embodiments, the bone implant is configured as a bone harvesting device to collect bone from the bone implant site.

FIG. 43 depicts a bone implant 1400, for example, a percutaneous pin, similar to the bone implants described above. The bone implant is cannulated 1402 and includes a threaded tip 1404. The threaded tip is an anchoring element for the bone implant and is configured in a similar manner to a bone tap. In some embodiments, the bone implant is cannulated for harvesting bone at the bone implant site.

FIG. 44 depicts a bone implant 1500, for example, a percutaneous pin, similar to the bone implants described above. The bone implant includes a head 1502, a body 1504 adjacent to the head and a tip 1506 opposite the head. The bone implant includes threading 1508 which can be an anchoring element of the bone implant. The bone implant is configured for engagement with navigation reference frame 28, described above and is configured to facilitate removal and attachment of navigation reference frame 28 without rotating the bone implant. The bone implant includes a screw or pin 1510 that is configured to prevent the bone implant from rotating. In some embodiments, the bone implant is cannulated.

Figures 45, 46, 47, 48, 49:
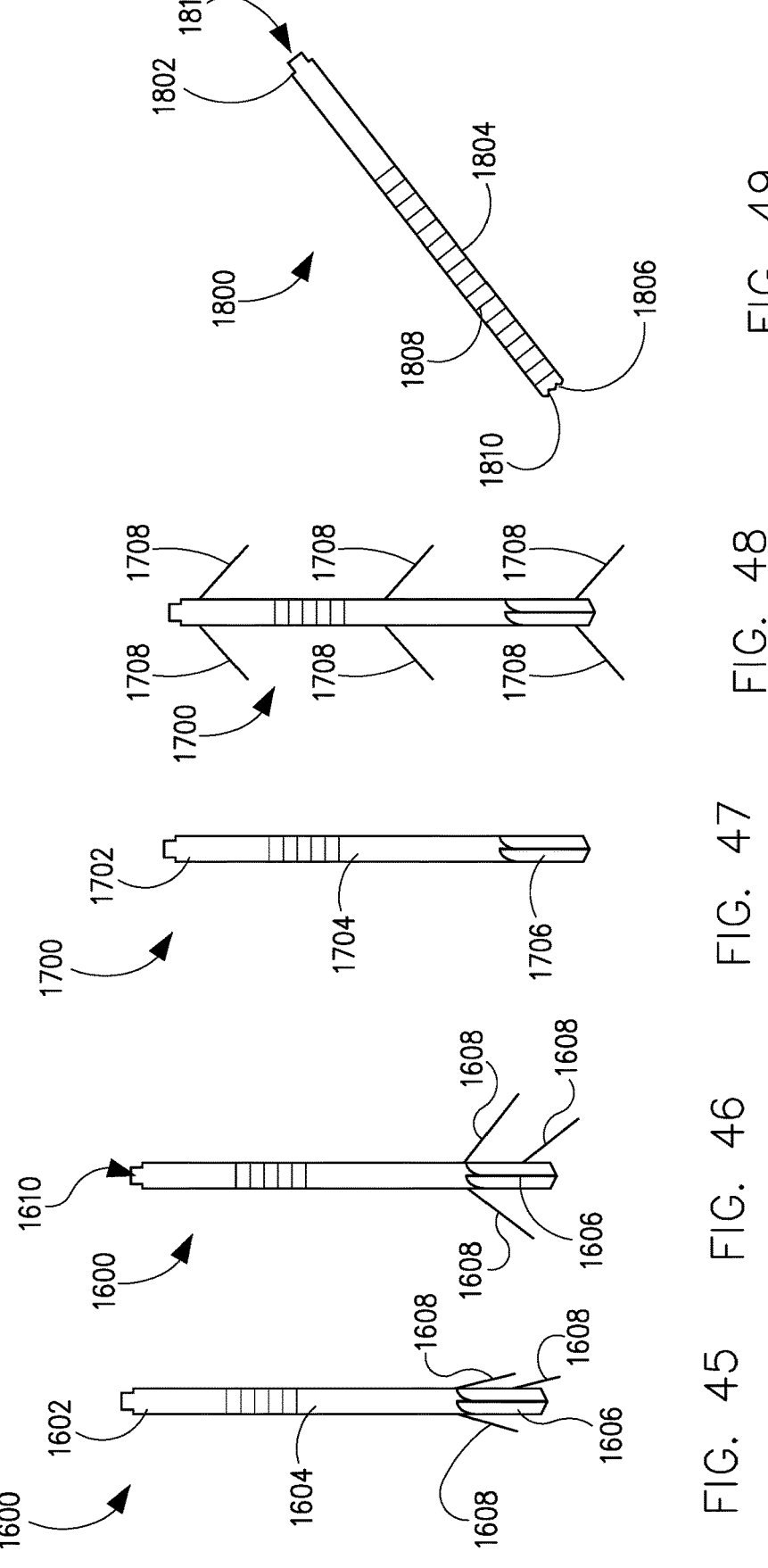
FIG. 45 is a side view of one embodiment of a bone implant for percutaneous use.
FIG. 46 is a side view of the bone implant of FIG. 45.
FIG. 47 is a side view of one embodiment of a bone implant for percutaneous use.
FIG. 48 is a side view of the bone implant of FIG. 47.
FIG. 49 is a perspective view of one embodiment of a bone implant for percutaneous use.

FIGS. 45-46 depict a bone implant 1600, for example, a percutaneous pin, similar to the bone implants described above. The bone implant includes a head 1602, a body 1604 adjacent to the head and a tip 1606 opposite the head. The bone implant includes an anchoring element, for example, pins 1608. The pins are configured to keep the bone implant upright and are configured to enhance grip of the bone implant at the bone implant site. The bone implant can be fixed before, during and/or after bone harvesting. The bone implant is cannulated 1610.

FIGS. 47-48 depict a bone implant 1700, for example, a percutaneous pin, similar to similar to bone implant 10 described above with regard to FIGS. 1-15. The bone implant includes a head 1702, a body 1704 adjacent to the head and a tip 1706 opposite the head. The bone implant includes an expandable member, including deployable claws 1708. The deployable claws contact the head, the body and the tip of the bone implant and are movable between an unexpanded configuration (FIG. 47) and expanded configuration (FIG. 48) when deployed at a bone implant site to fix and stabilize the bone implant at the bone implant site. The bone implant can be fixed before, during and/or after bone harvesting. In some embodiments, the bone implant is cannulated.

FIG. 49 depicts a bone implant 1800, for example, a percutaneous pin, similar to the bone implants described above. The bone implant includes a head 1802, a body 1804 adjacent to the head and a tip 1806 opposite the head. The bone implant includes threading 1808 and the tip includes a plurality of teeth 1810. The bone implant is canulated 1812 and is configured to dispose bone graft at a bone implant site before or after navigation has been implemented.

Figures 50, 51, 52, 53, 54, 55:
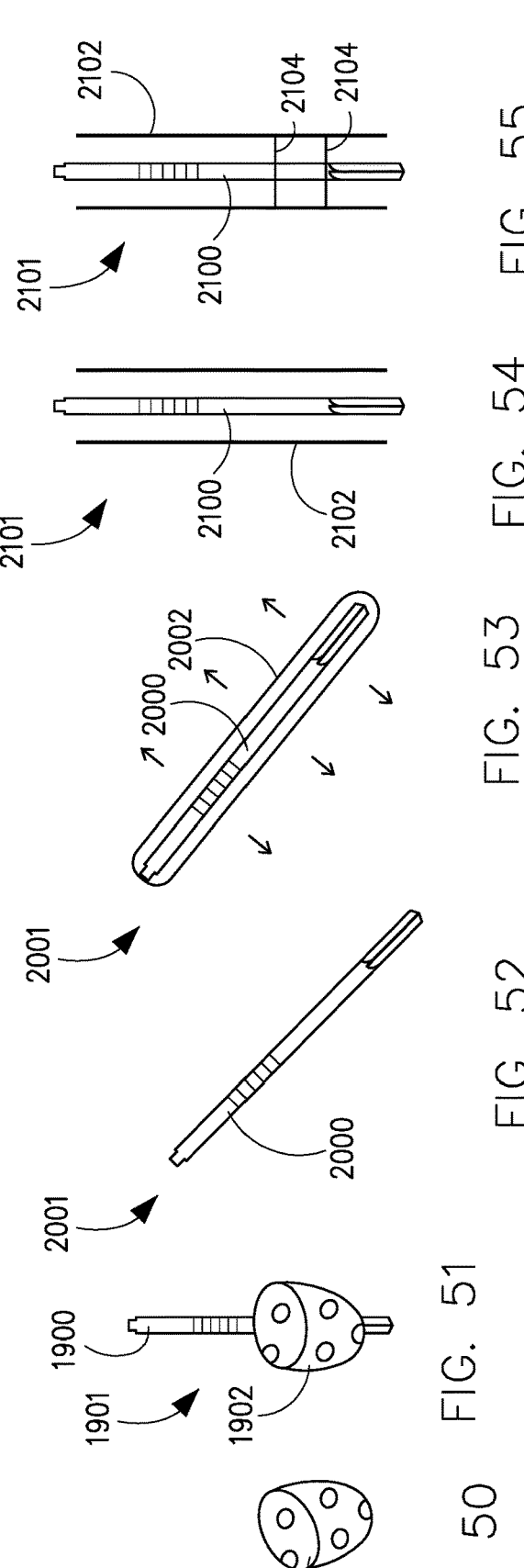
FIG. 50 is a side view of one embodiment of a surgical system for percutaneous use.
FIG. 51 is a side view of the surgical system of FIG. 50.
FIG. 52 is a perspective view of one embodiment of a surgical system for percutaneous use.
FIG. 53 is a perspective view of the surgical system of FIG. 52.
FIG. 54 is a side view of one embodiment of a surgical system for percutaneous use.
FIG. 55 is a side view of the surgical system of FIG. 54.

FIGS. 50-51 depict a surgical system 1901, including a bone implant 1900, for example, a percutaneous pin, similar to the bone implants described above. The system includes a jig box/acetabular shaped cup 1902. An opening (not shown) at the bone implant site is formed via a burr and the jig box/acetabular shaped cup is configured to harvest bone at the bone implant site. The bone implant is configured as an anchoring element to fix the jig box/acetabular shaped cup at the bone implant site and prevents rotation of the jig box/acetabular shaped cup.

FIGS. 52-53 depict a surgical system 2001, including a bone implant 2000, for example, a percutaneous pin, similar to the surgical system 101 and bone implant 100, as described above with regard to FIGS. 16-20. The system includes an expandable member, for example, a sheath or a sleeve 2002 configured for engagement with the bone implant. The sleeve is disposed in an opening (not shown) formed within a bone implant site. The bone implant is disposed within the sleeve to fix the bone implant with the opening. The sleeve is configured to provide stability to the bone implant at the bone implant site.

FIGS. 54-55 depict a surgical system 2101, including a bone implant 2100, for example, a percutaneous pin, similar to the surgical system 101 and bone implant 100, as described above with regard to FIGS. 16-20. The system includes a bone harvesting assembly, for example, a trocar 2102. The bone implant is configured for disposal within the trocar and expandable members, for example, deployable anchors 2104 are configured to deploy and engage with an opening (not shown) formed in a bone implant site to fix/stabilize the bone fastener with the bone implant site. The deployable anchors can be horizontal rods.

In some embodiments, a surgical system can include a plurality of varying sized bone implants, for example, percutaneous pins that can be sized up during a procedure after subsequent grafting has occurred. In some embodiments, a surgical system can include a bone harvesting device and a bone implant, including a percutaneous pin. The percutaneous pin can be larger in diameter than the bone harvesting device such that the bone implant can be disposed within an opening (not shown) used for bone harvesting at the bone implant site to fix the bone implant with the opening. In some embodiments, an adaptor can be used with the bone implant such that the bone implant can be disposed with the opening after the bone harvesting device harvests bone. In some embodiments, the bone implant can include various lengths. In some embodiments, the bone implant can include a shallow plate with a central canal configured for bone harvesting.

The bone implants and systems described above can be fabricated from biologically acceptable materials suitable for medical applications, including metals, synthetic polymers, ceramics and bone material and/or their composites. For example, the bone implants and systems, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the bone implants and the systems may have material composites, including the above materials, to achieve various desired characteristics such as strength, rigidity, elasticity, compliance, biomechanical performance, durability and radiolucency or imaging preference. The components of the bone implants and the systems, individually or collectively, may also be fabricated from a heterogeneous material such as a combination of two or more of the above-described materials. The components of the bone implants and the systems may be monolithically formed, integrally connected or include fastening elements and/or instruments, as described herein.

Bone Material

The bone material can be cancellous bone/trabecular bone that has been harvested from the bone implant site described above. The bone material can be natural bone, synthetic bone material (e.g., demineralized bone, ceramic, etc.) or a combination thereof that is solid or semi-solid. One type of bone material is demineralized bone matrix (DBM). In some embodiments, DBM compositions that allow osteogenesis, osteoinduction and/or osteoconduction are provided. DBM compositions are provided that allow osteogenesis, osteoinduction and/or osteoconduction. The DBM compositions provided, in some embodiments, are made from bone material that does not contain a binder.

In some embodiments, the DBM compositions are demineralized bone fibers are cartridge milled and have a ribbon-like shape and increased surface area. In some embodiments, bone material of milled and lyophilized demineralized bone fibers are cartridge milled fibers having a ribbon-like shape, increased surface area and a curled portion. In some embodiments, the bone material of milled and lyophilized demineralized bone fibers comprises autograft or allograft bone. In some embodiments, the bone fibers have a diameter from about 100 μm to about 2 mm. In some embodiments, the bone fibers have a length from about 0.5 mm to about 50 mm. In some embodiments, the bone fibers have an average length from about 0.5 cm to about 10 cm. In some embodiments, the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1.

In some embodiments, the bone fibers have a ribbon like shape and have increased surface area by from about 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 55.0, 60.0, 65.0, 70.0, 75.0, 80.0, 85.0, 90.0, 95.0, to about 100.0% when compared to bone chips, or powders.

In some embodiments, the bone material comprises cortical bone, cancellous bone, cortico-cancellous bone, or mixtures thereof. In some embodiments, the bone material is obtained from autogenous bone, allogeneic bone, xenogeneic bone, or mixtures thereof. In some embodiments, the bone material is lyophilized and shaped. In some embodiments, the shape of the lyophilized bone material is cube, square, triangle, rectangular, circular, disc or cylinder shape. In some embodiments, the shape of the lyophilized bone material is disc shaped and the disc has a reservoir configured to contact a liquid. In some embodiments, the shape of the lyophilized bone material is cylinder shaped. In some embodiments, the bone material has a plurality of channels running longitudinally through the center of the cylinder shaped bone material to allow fluid to hydrate the bone material. In some embodiments, the bone material has a plurality of channels running longitudinally through the exterior of the cylinder shaped bone material to allow fluid to hydrate the bone material. In some embodiments, the cylinder shaped bone material further comprises a plurality of channels running longitudinally through an exterior of the bone material to allow fluid to hydrate the bone material.

In some embodiments, the DBM includes particles that are non-fibrous. In some embodiments, the particles are powders, microspheres, sponges, pastes, gels, and/or granules. In one embodiment, the particles are powders.

In some embodiments, the DBM fibers comprise from about 1 to about 70 micrometers or from about 125 to about 250 micrometers. In some embodiments, the bone fibers include a length from about 100 micrometers to about 2 mm. In some embodiments, the bone fibers have a length from about 0.5 cm to about 10 cm, about 1 cm to about 8 cm, about 3 cm to about 5 cm, about 0.5 mm to about 50 mm, about 1.0 mm to about 25 mm, or about 5 mm to about 10 mm. The fibers include a diameter of about 100 micrometers to about 2 mm.

The fibers are milled in such a way as to provide increased surface area in a compact shape and size. In some embodiments, the fibers include a curled shape such that diameter of the curled fibers is between about 50 micrometers and about 3 mm, and the diameter of the fibers in a flattened configuration is about 125 micrometers to about 5 mm. In some embodiments, the fibers include a curled shape such that diameter of the curled fibers is between about 100 micrometers and about 1 mm, and the diameter of the fibers in a flattened configuration is about 250 micrometers to about 2 mm.

DBM fibers for use in the present disclosure can be obtained commercially or can be prepared by known techniques. In general, advantageous, osteoinductive DBM materials can be prepared by decalcification of cortical and/or cancellous bone fibers, often by acid extraction. The fibers can be milled for example cartridge milled. The acid extraction process can be conducted so as to leave collagen, noncollagenous proteins, and growth factors together in a solid fiber. Methods for preparing bioactive demineralized bone are described in U.S. Pat. Nos. 5,073,373; 5,484,601; and 5,284,655, as examples. DBM products are also available commercially, including for instance, from sources such as Regeneration Technologies, Inc. (Alachua, Fla.), The American Red Cross (Arlington, Va.), and others. Bone fibers that are solely osteoconductive can be prepared using similar techniques that have been modified or supplemented to remove or inactivate (e.g. by crosslinking or otherwise denaturing) components in the bone matrix responsible for osteoinductivity. Osteoinductive and/or osteoconductive DBM materials used in the present disclosure can be derived from human donor tissue, especially in regard to implant devices intended for use in human subjects.

In some embodiments, the bone fibers of allograft bone have an average length to average thickness ratio or aspect ratio of the fibers from about 50:1 to about 1000:1. In overall appearance the bone fibers can be in the form of ribbons, threads, narrow strips, and/or thin sheets. The elongated bone fibers can be substantially linear in appearance or they can be coiled to resemble springs. In some embodiments, the bone fibers have linear portions and coiled portions. In some embodiments, the bone fibers are of irregular shapes including, for example, linear, serpentine and/or curved shapes. In some embodiments, the fibers can be curled at the edges to have a substantially hemicircular cross-sections. In some embodiments, the fibers may be entirely or partially helical, circumvoluted or in the shape of a corkscrew. The elongated bone fibers can be demineralized however some of the original mineral content may be retained when desirable for a particular embodiment. The bone graft fiber may further comprise mineralized bone material.

The bone fiber sizes and shapes may be created in a number of ways, for example, through cartridge milling. One such example of a suitable cartridge mill is the Osteobiologic Milling Machine, as described in U.S. Patent Publication No. 2012/0160945, assigned to Warsaw Orthopedic, Inc. and is hereby incorporated by reference in its entirety. However, it is contemplated that the bone fibers may be alternatively milled using vices, cutters, rollers, rotating rasps or reciprocating blade mills.

Non-Bone Material Additives

In some embodiments, the bone material may be combined with non-bone material additives after demineralization and/or lyophilization and before implantation. For example, the bone material may be combined with a bioerodible polymer. The bioerodible polymer exhibits dissolution when placed in a mammalian body and may be hydrophilic (e.g., collagen, hyaluronic acid, polyethylene glycol). Synthetic polymers are suitable according to the present disclosure, as they are biocompatible and available in a range of copolymer ratios to control their degradation.

In some embodiments, hydrophobic polymers (e.g. poly (lactide-co-glycolyde), polyanhydrides) may be used. Alternatively, a combination of hydrophilic and hydrophobic polymers may be used in the bone material of the disclosure.

Exemplary materials may include biopolymers and synthetic polymers such as human skin, human hair, collagen, fat, thin cross-linked sheets containing fibers and/or fibers and chips, polyethylene glycol (PEG), chitosan, alginate sheets, cellulose sheets, hyaluronic acid sheet, as well as copolymer blends of poly (lactide-co-glycolide) PLGA.

In some embodiments, the particles disclosed herein can also include other biocompatible and bioresorbable substances. These materials may include, for example, natural polymers such as proteins and polypeptides, glycosaminoglycans, proteoglycans, elastin, hyaluronic acid, dermatan sulfate, gelatin, or mixtures or composites thereof. Synthetic polymers may also be incorporated into the bone material. These include, for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly (ethylene terephthalate), poly(butylene terephthalate), polyethylene glycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to previously-listed homo- and copolymers.

The bioerodible polymer may have a molecular weight of from about 1,000 to about 30,000 Daltons (Da). In various embodiments, the polymer may have a molecular weight of from about 2,000 to about 10,000 Da. In some embodiments, the polymer may have a molecular weight of from about 2,000 to 4,000 Da or from about 3,000 to 4,000 Da. In some embodiments, the bioerodible polymer may have a molecular weight of 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000 Da.

In some embodiments, the bioerodible polymer is collagen. Collagen has excellent histocompatibility without antibody formation or graft rejection. Any suitable collagen material may be used, including known collagen materials, or collagen materials as disclosed in U.S. patent application Ser. No. 12/030,181, filed Feb. 12, 2008, hereby incorporated by reference in its entirety. Various collagen materials can be used, alone or in combination with other materials.

Insoluble collagen material for use in the disclosure can be derived from natural tissue sources, (e.g. xenogeneic, allogeneic, or autogenic relative to the recipient human or other patient) or recombinantly prepared. Collagens can be subclassified into several different types depending upon their amino acid sequence, carbohydrate content and the presence or absence of disulfide cros slinks. Types I and III collagen are two of the most common subtypes of collagen and may be used in the present disclosure. Type I collagen is present in skin, tendon and bone, whereas Type III collagen is found primarily in skin. The collagen used in compositions of the disclosure can be obtained from skin, bone, tendon, or cartilage and purified by methods well known in the art and industry. Alternatively, the collagen can be purchased from commercial sources.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from Collagen Matrix Inc. (Allendale, NJ), or Kensey Nash Corporation (Exton, Pa.), which manufactures a fibrous collagen known as Semed F, from bovine hides. Collagen materials derived from bovine hide are also manufactured by Integra Life Science Holding Corporation (Plainsboro, N.J.). Naturally derived or recombinant human collagen materials are also suitable for use in the disclosure. Illustratively, recombinant human collagen products are available from Fibrogen, Inc. (San Francisco, Calif.).

In some embodiments, the bone material can be combined with synthetic ceramics that are effective to provide a scaffold for bone growth and which are completely bioresorbable and biocompatible. The synthetic ceramics should provide high local concentrations of calcium, phosphate and silicon ions that act as a nidus for de-novo bone formation. The use of such a resorbable ceramics provides many advantages over alternative conventional materials. For instance, it eliminates the need for post-therapy surgery for removal and degrades in the human body to biocompatible, bioresorbable products.

In some embodiments, the synthetic ceramics disclosed herein may be selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride (Si3N4), and biocompatible ceramics may be used. In some embodiments, the ceramic is tri-calcium phosphate or biphasic calcium phosphate and silicon ceramics. In some embodiments, the ceramic is tricalcium phosphate.

In some embodiments, the ceramics are a combination of a calcium phosphate ceramic and a silicon ceramic. In some embodiments, the calcium phosphate ceramic is resorbable biphasic calcium phosphate (BCP) or resorbable tri-calcium phosphate (TCP), most preferably resorbable TCP.

Biphasic calcium phosphate can have a tricalcium phosphate:hydroxyapatite weight ratio of about 50:50 to about 95:5, about 70:30 to about 95:5, about 80:20 to about 90:10, or about 85:15. The mineral material can be a granular particulate having an average particle diameter between about 0.2 and 5.0 mm, between about 0.4 and 3.0 mm, or between about 0.4 and 2.0 mm.

The ceramics of the disclosure may also be oxide ceramics such as alumina (Al2O3) or zirconia (ZrO2) or composite combinations of oxides and non-oxides such as silicon nitride).

In some embodiments, a binding agent may be added to the bone material before implantation. Examples of suitable binding agents that optionally can be include, but are not limited to: (i) Polyhydroxy compound, for example, such classes of compounds as the acyclic polyhydric alcohols, non-reducing sugars, sugar alcohols, sugar acids, monosaccarides, disaccharides, water-soluble or water dispersible oligosaccarides, polysaccarides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing.

In some embodiments, the composition containing the fibers may also contain other beneficial substances including for example preservatives, cosolvents, suspending agents, viscosity enhancing agents, ionic strength and osmolality adjusters and/or other excipients. Suitable buffering agents can also be used an include but are not limited to alkaline earth metal carbonates, phosphates, bicarbonates, citrates, borates, acetates, succinates, or others. Illustrative-specific buffering agents include for instance sodium phosphate, sodium citrate, sodium borate, sodium acetate, sodium bicarbonate, sodium carbonate, and sodium tromethanine (TRIS).

One of more biologically active ingredients may be added to the resulting bone material (e.g., lyophilized bone fibers). These active ingredients may or may not be related to the bone repair capabilities of the composition. Suitable active ingredients hemostatic agents, bone morphogenic proteins (BMPs), genes, growth differentiation factors (GDFs), or other non-collagenic proteins such as TGF-β, PDGF, ostropontin, osteonectin, cytokines, and the like.

In one embodiment, the bone material may include at least one BMPs, which are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In some embodiments, the bone material contains other bioactive agents which can be delivered with the bone material of the disclosure. In certain embodiments, the bioactive agent is a drug. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergic, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, antiarthritics, and diagnostic agents.

A more complete listing of bioactive agents and specific drugs suitable for use in the present disclosure may be found in "The Merck Index: An Encyclopedia of Chemicals, Drugs, and Biologicals," Edited by Susan Budavari, et al.; and the United States Pharmacopoeia/National Formulary XXXVII/XXXII, published by the United States Pharmacopeial Convention, Inc., Rockville, MD, 2013, each of which is incorporated herein by reference.

Bioactive agents may also be provided by incorporation into the bone material. Bioactive agents such as those described herein can be incorporated homogeneously or regionally into the implant material by simple admixture or otherwise. Further, they may be incorporated alone or in conjunction with another carrier form or medium such as microspheres or another microparticulate formulation. Suitable techniques for forming microparticles are well known in the art and can be used to entrain or encapsulate bioactive agents, whereafter the microparticles can be dispersed within the bone material upon or after its preparation.

It will be appreciated that the amount of additive used will vary depending upon the type of additive, the specific activity of the particular additive preparation employed, and the intended use of the composition. The desired amount is readily determinable by the user.

Any of a variety of medically and/or surgically useful substances can be incorporated in, or associated with, the allograft bone material either before, during, or after preparation of the bone material. Thus, for example when the non-allograft bone material is used, one or more of such substances may be introduced into the bone fibers, for example, by soaking or immersing these bone fibers in a solution or dispersion of the desired substance(s).

In some embodiments, the bone material can be lyophilized with one or more growth factors (e.g., BMP, GDF, etc.), drugs so that it can be released from the bone material in a sustained release manner.

Methods of Using a Percutanous Bone Implant

In some embodiments, a method of using a percutaneous implant during a bone harvesting procedure is provided, as shown in FIGS. 56-59. In some embodiments, the bone harvesting is performed concurrently with a minimally invasive surgical navigation guided procedure. The bone harvesting can be performed at a bone implant site, for example, an iliac crest of a patient, as shown in FIG. 56. The method comprises forming an opening, for example, opening 48, at a bone harvesting site (FIG. 57); harvesting the bone at the bone harvesting site from the opening via a bone harvesting tool 50 (FIG. 58); removing the bone harvesting tool from the opening; inserting a bone implant within the opening (FIG. 59), the bone implant comprising a head, a body adjacent to the head and a tip opposite the head, at least the head, body or tip configured to contact bone, and an expandable member contacting at least one of the head, tip or body; and moving the expandable member from an unexpanded configuration to an expanded configuration to fix the bone implant with the opening. In some embodiments, the expandable member is configured to anchor the bone implant at the bone implant site. In some embodiments, the expandable member includes at least one wing configured to anchor the bone implant at the bone implant site in the expanded configuration. In some embodiments, the opening is created via the bone harvesting tool 50. In some embodiments, the bone implant described above includes bone implant 10 and/or bone implant 100.

In some embodiments, the bone implant provides fixation and stability at the bone implant site before, during and/or after a bone harvesting procedure is performed. In some embodiments, the bone implant reduces the number of openings created in a patient during a bone harvesting procedure. In some embodiments, the method includes implementing surgical navigation for preforming the bone harvesting procedure, as shown in FIG. 56. In some embodiments, the bone implant is a percutaneous pin that is configured to fix the navigation reference frame 28 to a bone implant site, for example, the opening, and is configured to harvest bone simultaneously. In some embodiments, the navigation reference frame 28 can be attached to the body or the head of the bone implant, as shown in FIG. 56. See, for example, similar surgical navigation components and their use as described in U.S. Pat. Nos. 6,021,343, 6,725,080, 6,796,988, the entire contents of each of these references being incorporated by reference herein. Exemplary tracking systems are also disclosed in U.S. Pat. Nos. 8,057,407, 5,913,820, 5,592,939, the entire contents of each of these references being incorporated by reference herein.

Methods of Treatment

Illustrative bone implants that can be fixed to the bone implant sites of the disclosure include, for instance, those resulting from bone harvesting, injury, defects brought about during the course of surgery, infection, malignancy or developmental malformation. The bone implants can be used in a wide variety of orthopedic, periodontal, neurosurgical and oral and maxillofacial surgical procedures including, but not limited to the bone harvesting and/or repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be harvested from and/or repaired or replaced with the bone implant include, but are not limited to the iliac crest, ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

Kits

The present application also provides a medical kit for bone harvesting at a bone implant site, the kit including at least a bone implant and/or surgical system, as described above and a package enclosing the bone implant and/or surgical system in a sterile condition. Such kits can include one or more of the bone implants described above, a bone harvesting device, for example, a trocar as described above, and a surgical instrument, for example, a drill, a tap, a driver, and/or a dilator.

It should be understood that the forgoing relates to exemplary embodiments of the disclosure and that modifications may be made without departing from the spirit and scope of the disclosure as set forth in the following claims.

What is claimed is:

1. A bone implant for percutaneous use, the bone implant comprising a head, a body adjacent to the head and a tip opposite the head, at least the head, body or tip configured to contact bone, and an expandable member adjacent to the tip, the expandable member movable from an unexpanded configuration to an expanded configuration when deployed at a bone implant site, wherein the expandable member comprises wings extended from the body toward the tip such that the wings and the tip join to form an acute angle at a juncture of the wings and the tip, wherein each of the wings comprises a proximal end adjacent to the body and a distal end away from the body, each of the wings comprising a circular opening disposed at the distal end of each of the wings and the tip also comprises a proximal end adjacent to the body and a distal end away from the body, the tip comprising a circular opening disposed at the distal end of the tip, the circular opening of each of the wings and the circular opening of the tip configured to collect bone from the bone implant site, and the bone implant site includes a bone harvesting site and the bone implant is configured to anchor at the bone harvesting site before, during or after bone is harvested such that the bone collected is removed from the bone harvesting site.

2. The bone implant according to claim 1, wherein the bone implant is anchored to the bone implant site when the expandable member is in the expanded configuration.

3. The bone implant according to claim 1, wherein the bone implant is a cannulated percutaneous pin and at least a portion of the bone implant is threaded.

4. The bone implant according to claim 1, wherein the wings are configured to anchor the bone implant at the bone implant site in the expanded configuration.

5. A bone implant for percutaneous use, the bone implant comprising a head, a body adjacent to the head and a tip opposite the head, at least the head, body or tip configured to contact bone, and an anchoring element adjacent to the tip configured to fix the bone implant to a bone implant site, wherein the anchoring element comprises wings extended from the body toward the tip such that the wings and the tip join to form an acute angle at a juncture of the wings and the tip, wherein each of the wings comprises a proximal end adjacent to the body and a distal end away from the body, each of the wings comprising a circular opening disposed at the distal end of each of the wings; and the tip also comprises a proximal end adjacent to the body and a distal end away from the body, the tip comprising a circular opening disposed at the distal end of the tip, the circular opening of each of the wings and the circular opening of the tip configured to collect bone from the bone implant site and the wings and the tip are configured to fix the bone implant to the bone implant site for collecting bone from the bone implant site, wherein the bone implant site includes a bone harvesting site and the bone implant is configured to anchor at the bone harvesting site before, during or after bone is harvested such that the bone collected is removed from the bone harvesting site.

6. The bone implant according to claim 5, wherein at least a portion of the bone implant is threaded.

7. The bone implant according to claim 5, wherein an end of the tip has a plurality of teeth.

8. A surgical system for percutaneous bone harvesting, the system comprising a bone implant comprising a head, a body adjacent to the head and a tip opposite the head, and an expandable member having an interior and an exterior, the exterior of the expandable member configured to contact bone at a bone implant site, wherein the exterior of the expandable member comprises wings extended from the body toward the tip such that the wings and the tip join to form an acute angle at a juncture of the wings and the tip, wherein each of the wings comprises a proximal end adjacent to the body and a distal end away from the body, each of the wings comprising a circular opening disposed at the distal end of each of the wings; and the tip also comprises a proximal end adjacent to the body and a distal end away from the body, the tip comprising a circular opening disposed at the distal end of the tip, the circular opening of each of the wings and the circular opening of the tip configured to collect bone from the bone implant site, and the bone implant site includes a bone harvesting site and the bone implant is configured to anchor at the bone harvesting site before, during or after bone is harvested such that the bone collected is removed from the bone harvesting site.

* * * * *